(12) United States Patent
Rutherford et al.

(10) Patent No.: US 9,086,386 B1
(45) Date of Patent: Jul. 21, 2015

(54) SENSOR COUPLING APPARATUS

(75) Inventors: Paul S. Rutherford, Maple Valley, WA (US); Gary E. Georgeson, Tacoma, WA (US)

(73) Assignee: The Boeing Company, Chicago, IL (US)

(*) Notice: Subject to any disclaimer, the term of this patent is extended or adjusted under 35 U.S.C. 154(b) by 348 days.

(21) Appl. No.: 13/547,190

(22) Filed: Jul. 12, 2012

(51) Int. Cl.
*G01N 27/90* (2006.01)
*G01N 29/24* (2006.01)

(52) U.S. Cl.
CPC .............. *G01N 27/902* (2013.01); *G01N 29/24* (2013.01)

(58) Field of Classification Search
CPC . G01N 27/90; G01N 27/9006; G01N 27/902; G01N 29/24
USPC .............. 73/583, 635, 640, 661, 865.8, 866.5
See application file for complete search history.

(56) References Cited

U.S. PATENT DOCUMENTS

| | | | | |
|---|---|---|---|---|
| 3,534,591 A | * | 10/1970 | Phelan | 73/634 |
| 4,625,165 A | * | 11/1986 | Rothstein | 324/220 |
| 4,643,029 A | * | 2/1987 | Klinvex | 73/632 |
| 4,710,710 A | * | 12/1987 | Flora et al. | 324/220 |
| 5,207,005 A | * | 5/1993 | Amos et al. | 33/501.04 |
| 6,619,118 B1 | * | 9/2003 | Keck | 73/304 C |
| 7,340,971 B2 | * | 3/2008 | Carter et al. | 73/865.9 |
| 7,659,715 B2 | * | 2/2010 | Briffa et al. | 324/228 X |
| 8,109,160 B2 | | 2/2012 | Bossi et al. | |
| 2009/0307918 A1 | * | 12/2009 | Rogers et al. | 73/866.5 X |

FOREIGN PATENT DOCUMENTS

| | | | | | |
|---|---|---|---|---|---|
| CH | 599533 A | * | 5/1978 | | 73/865.8 |
| EP | 487253 A1 | * | 5/1992 | | G01N 27/90 |
| JP | 57106476 A | * | 7/1982 | | 219/124.34 |
| JP | 06268034 A | * | 9/1994 | | H01L 21/66 |
| JP | 07035808 A | * | 2/1995 | | G01R 31/02 |
| JP | 2010025801 A | * | 2/2010 | | G01N 27/90 |
| SU | 728115 A1 | * | 4/1980 | | G05B 23/02 |

* cited by examiner

*Primary Examiner* — Thomas P Noland
(74) *Attorney, Agent, or Firm* — Matthew W. Witsil; Moore & Van Allen PLLC (57) ABSTRACT

An inspection apparatus for nondestructive inspection/evaluation. The inspection apparatus may include a probe, and sensor, and a biasing spring. The probe may have a first end and a second, free end defining an opening. The sensor may be received in the opening. The biasing spring may be received in the opening in between the first end of the probe and the sensor to urge the sensor away from the first end of the probe. The probe may include a gimbal joint or ball and socket type joint and a spindle, where the joint provides for deflection of the probe relative to the spindle. A blocking pin for limiting the range of movement of the sensor retains part of the sensor in the opening. The sensor may have a position extending out of the opening, and a position where an end of the sensor is substantially flush with the end of the probe.

20 Claims, 9 Drawing Sheets

SENSOR COUPLING APPARATUS

GOVERNMENT RIGHTS

This invention was made with Government support under Contract No. FA8650-08-C-5213 awarded by the Department of Defense. The Government has certain rights in this invention.

FIELD

The present disclosure relates to nondestructive inspection/evaluation (NDI/NDE), and more particularly to sensors used in NDI/NDE that detect defects in structures and parts.

BACKGROUND

Increases in the complexity of aerospace structures have made NDI/NDE, which terms are used interchangeably herein, more and more difficult to apply successfully and cost-effectively. Often, a region of a particular structure requires inspection, but is inaccessible for the application of conventional NDE methods. In some cases such inspection requirements of regions with limited access have prompted part removal to improve access, or expensive redesigns altogether. Conventional tools include extenders and manipulation arms to reach into limited access areas and to aid probe placement on or near limited access areas of aircraft. Such areas may be cavities or obstructed areas, and include, for example, the interior of aircraft wings.

When in operation, certain sensors for detection of defects in a surface are preferably seated on the surface, or at least require maintaining no more than a maximum clearance from the surface. When a sensor, for example an eddy current sensor, is not completely seated on the surface, which may be referred to as "lift-off," the result may be a reduced sensitivity to small cracks.

A sensor may be applied to a surface that is not completely flat and require movement of the probe along the surface, or may be mounted to a rotating end of a probe for NDE in limited access areas. Either case may result in lift-off. For the rotating application, if the probe end is not exactly perpendicular to the surface to be inspected, the rotating path of the sensor will be eccentric; although the sensor may be flush with the surface at one point along the path, at an opposite point on the path there will be lift-off. Accordingly, apparatus is needed that addresses lift-off to provide adequate sensitivity for detection of defects over the full range of motion of the sensor.

SUMMARY

In accordance with an embodiment, an inspection apparatus may include a probe, and sensor, and bias means. The probe may have a first end and a second, free end defining an opening. The sensor may be received in the opening. The bias means may be received in the opening in between the first end of the probe and the sensor to urge the sensor away from the first end of the probe.

In accordance with another embodiment, an inspection apparatus may include a probe, a sensor, bias means, and means for limiting the range of movement of the sensor. The probe may have a longitudinal axis, a first end, and a second, free end having a surface and defining an opening, and may include a gimbal joint or ball and socket type joint disposed between the first end and the second, free end of the probe. The probe may further include a spindle having a proximal end and a distal end, with the distal end being operatively connected to the joint. The sensor may have a first end and a second end and be received in the opening, where the sensor has a range of movement relative to the probe. The bias means may be received in the opening in between the first end of the probe and the first end of the sensor to urge the sensor away from the first end of the probe. The means for limiting the range of movement of the sensor may retain part of the sensor in the opening. The sensor may have an extended position with the second end of the sensor extending away from the surface of the second, free end of the probe a predetermined distance, and a retracted position with the second end of the sensor substantially flush with the surface of the second, free end of the probe.

In accordance with another embodiment, a method performing an inspection is provided. The method includes providing a probe having a longitudinal axis and including a first end and a second, free end defining an opening, with bias means first inserted in the opening and then a sensor inserted in the opening. The sensor is urged away from the first end of the probe using the bias means, and the probe is rotated about the longitudinal axis.

Other aspects and features of the present disclosure, as defined solely by the claims, will become apparent to those ordinarily skilled in the art upon review of the following non-limited detailed description of the disclosure in conjunction with the accompanying figures.

BRIEF DESCRIPTION OF THE SEVERAL VIEWS OF THE DRAWINGS

The following detailed description of embodiments refers to the accompanying drawings, which illustrate specific embodiments of the disclosure. Other embodiments having different structures and operations do not depart from the scope of the present disclosure.

DESCRIPTION

The following detailed description of embodiments refers to the accompanying drawings, which illustrate specific embodiments of the disclosure. Other embodiments having different structures and operations do not depart from the scope of the present disclosure. Like reference numerals may refer to the same element or component in the different drawings.

Certain terminology is used herein for convenience only and is not to be taken as a limitation on the embodiments described. For example, words such as "proximal", "distal", "top", "bottom", "upper," "lower," "left," "right," "horizontal," "vertical," "upward," and "downward" merely describe the configuration shown in the figures or relative positions. The referenced components may be oriented in any direction and the terminology, therefore, should be understood as encompassing such variations unless specified otherwise.

Figure 1:
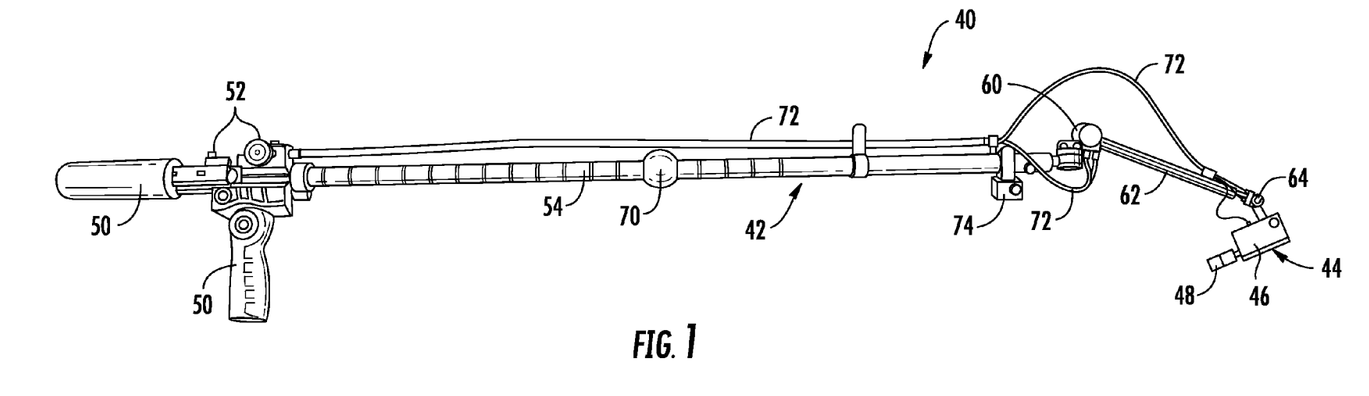
FIG. 1 is a side view of an example of a manipulator arm for NDE including a scanner with a probe in accordance with an embodiment of the present disclosure.

FIG. 1 shows an example of a device 40 for performing NDE in a limited access area, which may be referred to as extended reach NDE, limited access NDE, surgical NDE, or the like. The device 40 may include an articulating manipulator arm 42 with an end effector 44 provided at the distal end. In the embodiment shown, the end effector includes a scanner 46 and a probe 48. The probe 48 may include, for example, an eddy current sensor, a magnetic sensor, an ultrasonic sensor, or the like. For the embodiment shown, starting at the proximal end of the arm 42 may be operator handles 50, control knobs and switches 52, and a main shaft 54 with a proximal end mounted to the handles 50. A multi-axis elbow joint 60 may be mounted to the distal end of the main shaft 54, and a pivoting shaft 62 may be mounted to the multi-axis elbow joint 60. To provide an additional degree of articulation a wrist joint 64 may be mounted to the distal end of the pivoting shaft 62. A slider ball 70 may be provided on the main shaft to bear against the wall of the enclosure that contains the area to be inspected as the main shaft 54 extends through an access hole. The slider ball 70 provides a location for an operator to steady the arm 42. Control cables 72 may extend from the control knobs and switches 52 to the multi-axis elbow joint 60 and to the wrist joint 64. A video camera 74 may be mounted near the distal end of the main shaft 54 for situational awareness to aid the operator in placement of the distal end of the device 40 and the probe 48.

Figure 2:
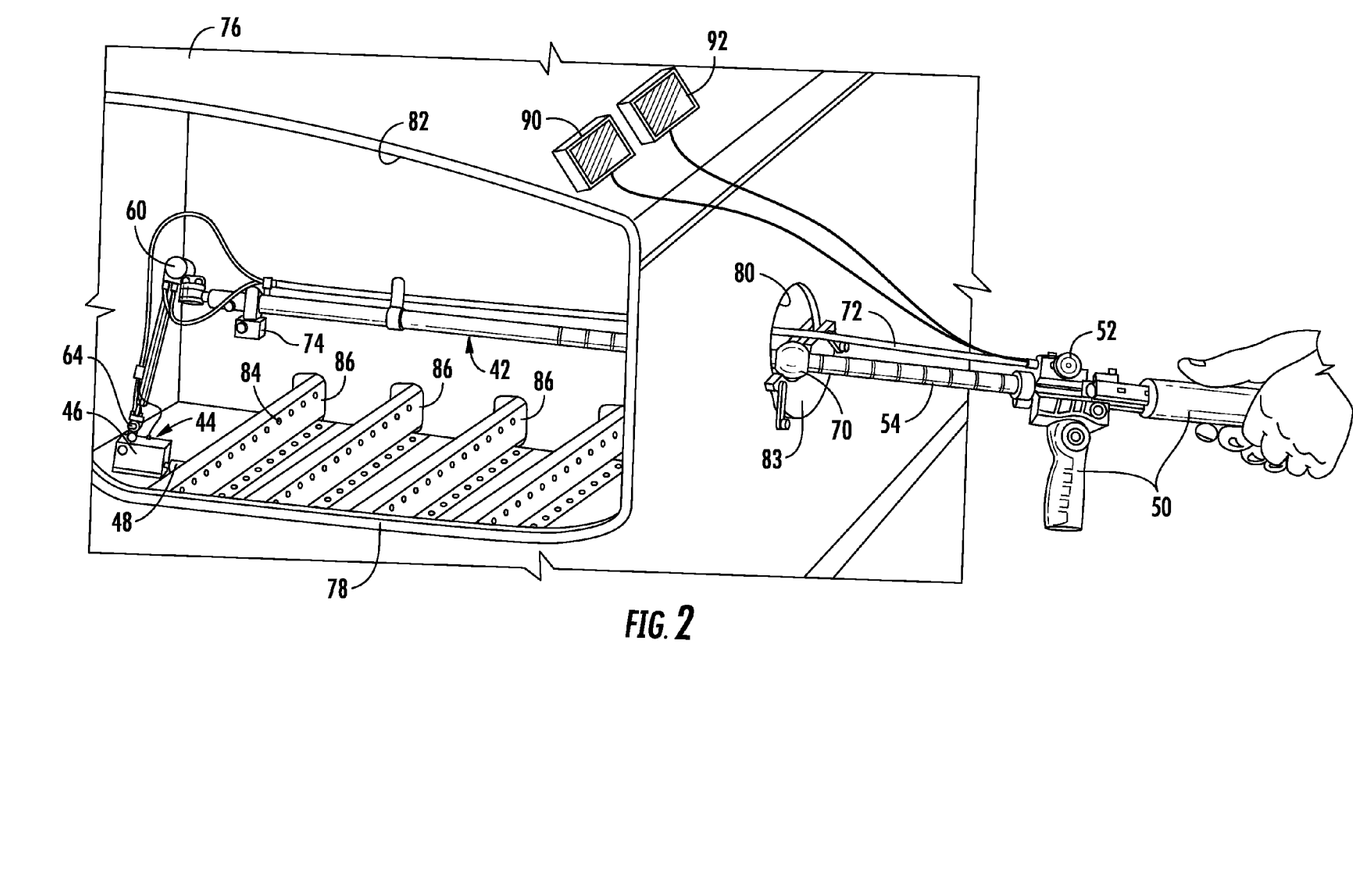
FIG. 2 is a perspective view of an exposed interior of a wing illustrating application of the exemplary manipulator arm of FIG. 1.

FIG. 2 shows a section of an aircraft wing 76 with an internal wall 78 cut away to expose the example NDE device of FIG. 1 in use. The device 40 extends through the access hole 80 into the enclosure 82, which is large enough for the distal end of the manipulator arm 42 and the end effector 44 to pass through, which in one embodiment is approximately three inches in diameter. A support bracket 83 is mounted in the opening 80. This embodiment of a support bracket 83 is semi-circular and defines a semi-circular opening to receive the slider ball 70. Levers may be rotated to turn bolts that extend through holes that are used to mount an access panel, which has been removed. In this example, the probe 48 is being used to detect defects in a structure or part, which may also be referred to as a target, which as shown is metal around fasteners 84 in stringers 86, specifically the metal around the bolts and nuts that are on the inboard side of the stringers 86. Other locations of inspection and other types of materials and structures or parts may be inspected as well. The pivoting shaft 62 is pivoted with the multi-axis elbow joint 60 to position the probe 48 behind the stringer 86 to be inspected, and the wrist joint 64 is pivoted to align the probe 48 with a bolt. Monitors 90, 92 are provided to assist the operator/inspector. One monitor 90 displays a high frequency eddy current impedance plane display, discussed in detail below and the other monitor 92 shows video.

Figure 3:
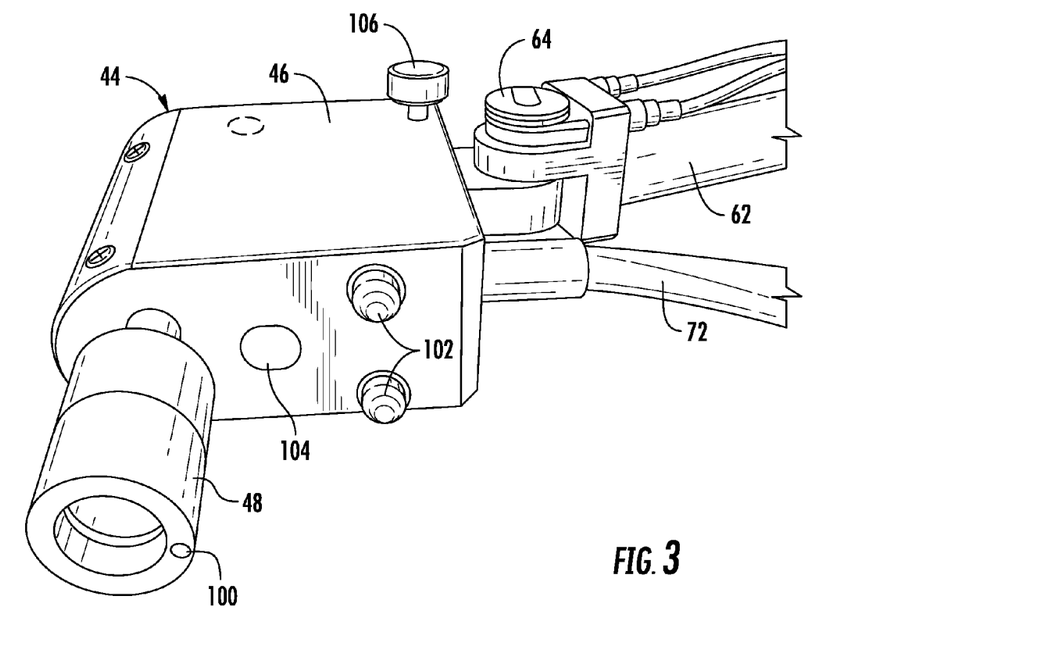
FIG. 3 is a front end perspective view of an example of a scanner including a probe in accordance with an embodiment of the present disclosure.
Figure 4:
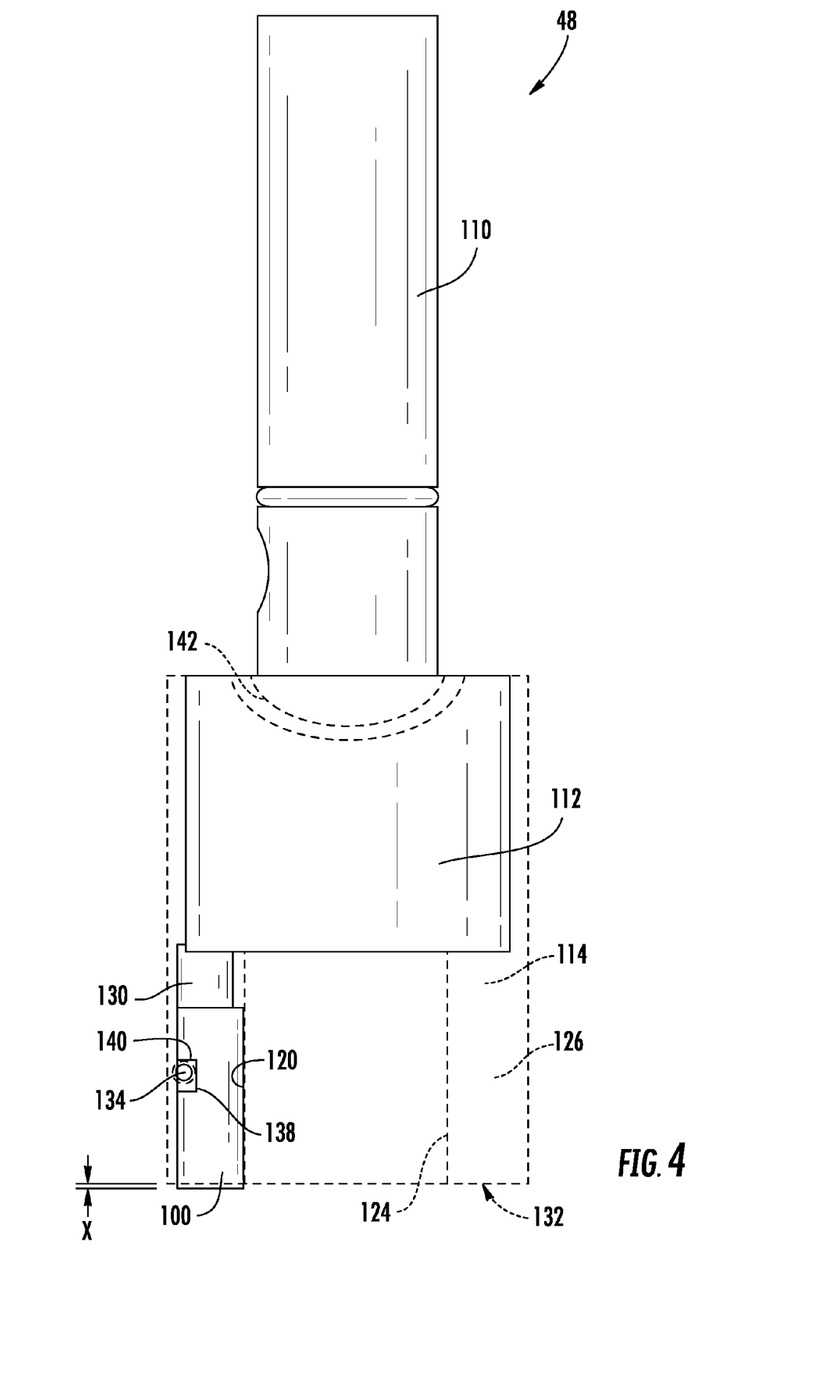
FIG. 4 is a side view of an example of a probe in accordance with an embodiment of the present disclosure.
Figure 5:
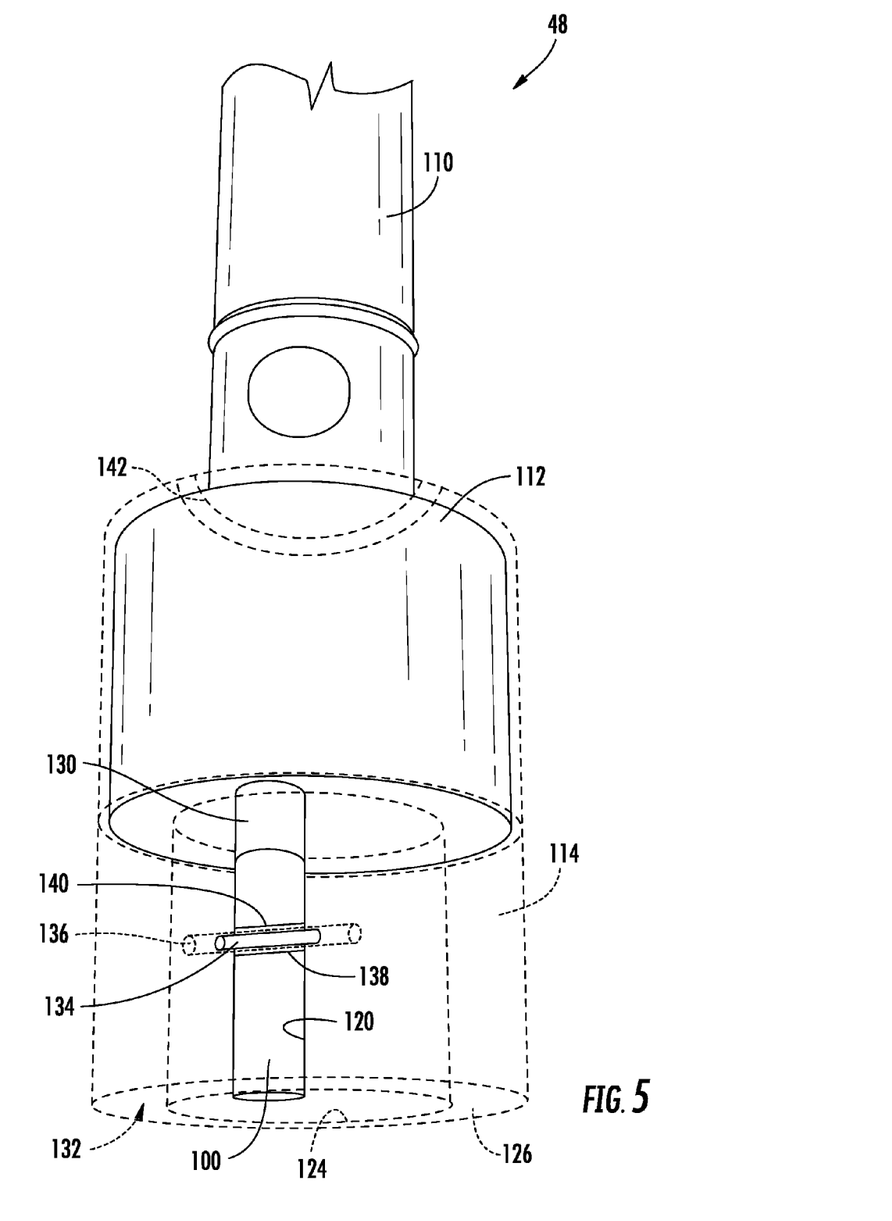
FIG. 5 is a side perspective view of the exemplary probe of FIG. 4.

FIG. 3 is an end perspective view of the end effector 44, which includes an embodiment of a probe 48 mounted to the scanner 46. In this embodiment the probe 48 may include an eddy current sensor 100, including a coil of wire. The scanner 46 may be a micro eddy current rotating scanner, which may include a motor. It is not necessary for other embodiments of the device 40 or the probe 48 that the scanner 46 be a rotating type. The distal end of the scanner 46 may include lights 102, for example LEDs, to illuminate the enclosure and the target to be inspected, and a camera lens 104 to provide an image to a video camera in the scanner 46. Another video camera could also be mounted in proximity of the probe 48 to provide additional situational awareness. A knob 106 has a threaded bolt (not shown) on it that may be loosened to remove the scanner 46 from the wrist joint 64. The other end of the threaded bolt may bear against a cylinder to which the scanner 46 is attached.

Figure 6:
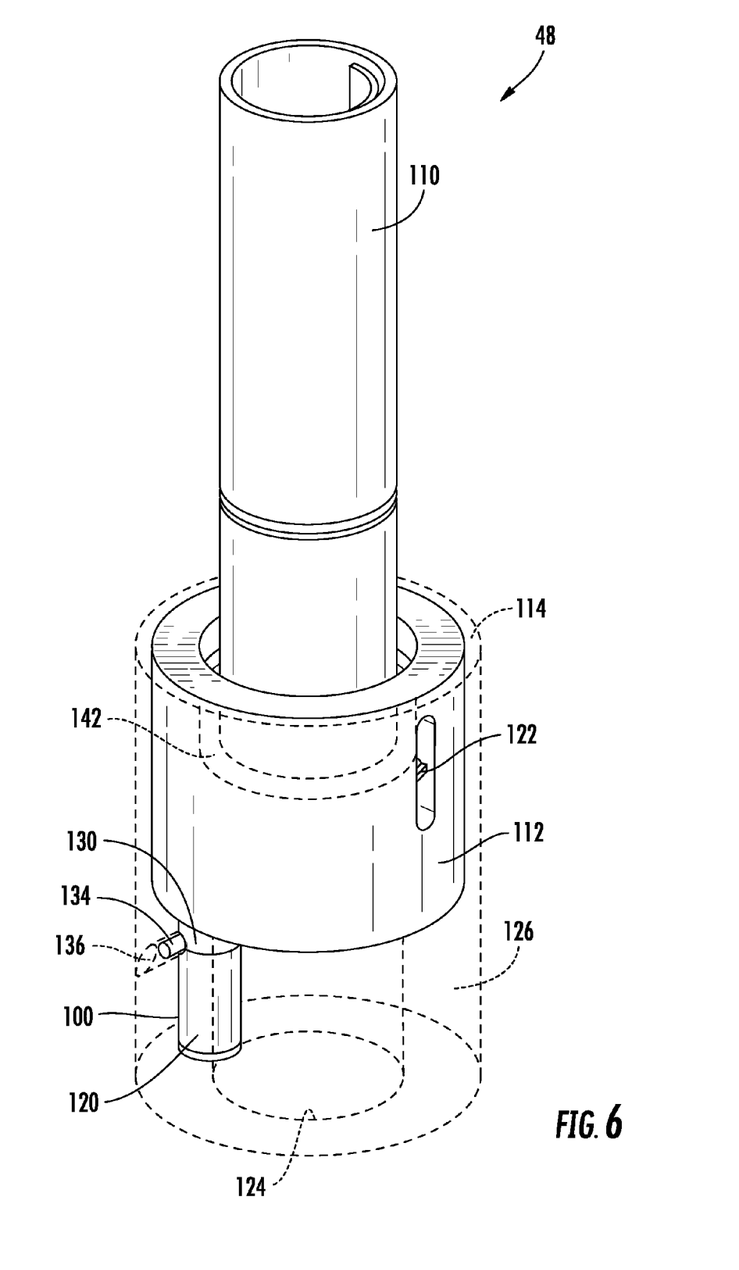
FIG. 6 is another side perspective view of the exemplary probe of FIG. 4.
Figure 7:
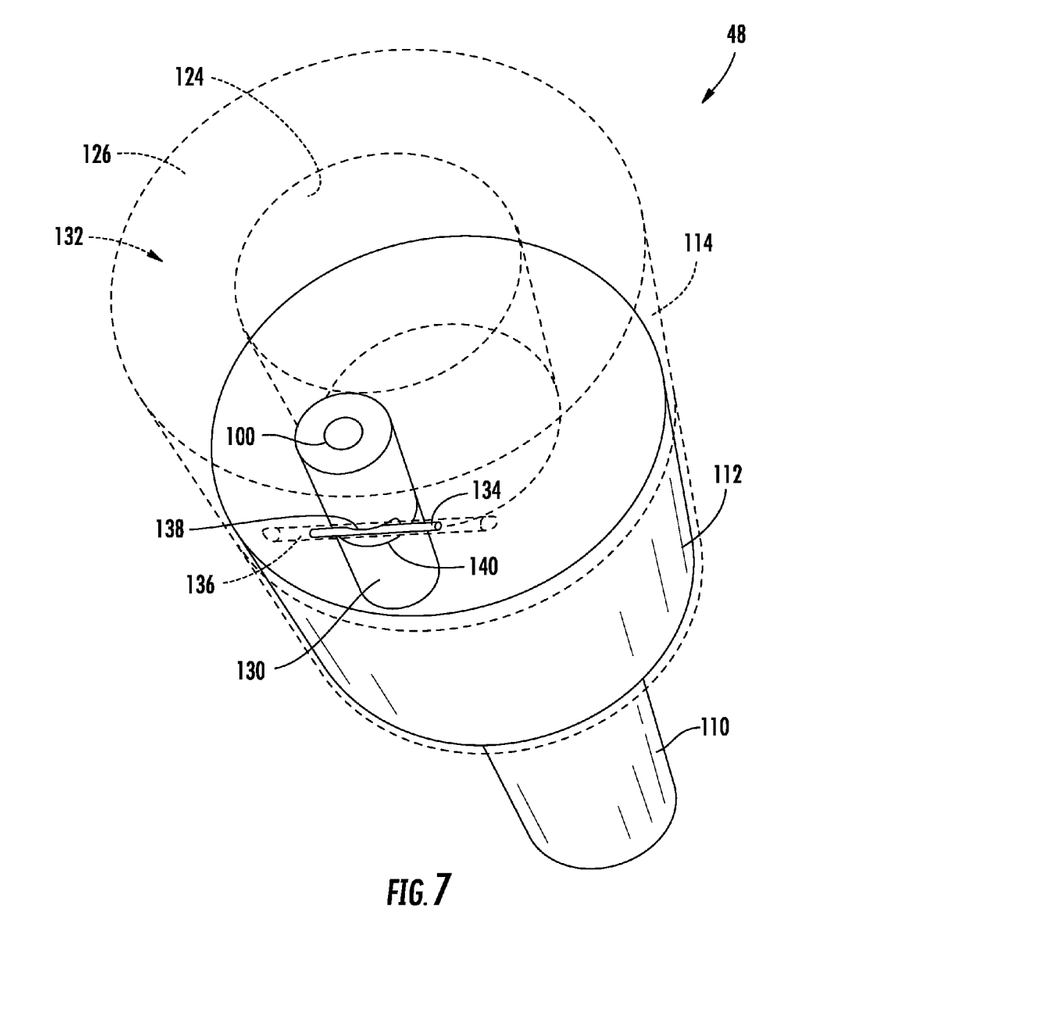
FIG. 7 is a bottom perspective view of the exemplary probe of FIG. 4.

FIGS. 4-7 show an embodiment of the probe 48 with an embodiment of an eddy current sensor 100. The probe 48 may include a spindle 110, a central member 112 mounted to the spindle 110, and a housing 114 mounted to the central member 112. In this embodiment, the housing 114 is translucent. The sensor 100 may be received in an opening which may be a bore 120 in the housing 114 or be otherwise slidably mounted to the housing 114. The central member 112 may be mounted to the spindle 110 with a set screw 122 (FIG. 6). The housing 114 may be cylindrical, may encase the sides of the central member 112, and extends distally below the bottom of the central member 112. Below the distal end of the central member 112 the housing 114 may define a substantially cylindrical opening 124 and have a cylindrical wall 126. The cylindrical wall 126 may be of adequate thickness to receive the sensor 100 in the bore 120 in the wall 126, as shown, or other configurations may be provided to attach the sensor 100 to the probe 48. In the example shown of inspecting the metal around a fastener 84, the opening 124 in the housing 114 is large enough to receive the end of the fastener 84 that protrudes from the structure.

A spring 130, such as a coil spring as schematically shown, a leaf spring, compressible and resilient material, or other biasing means may be provided in between the proximal end of the bore 120 and the proximal end of the sensor 110, and urges the sensor 100 distally such that the sensor 100 may extend out of the bore 120 past the distal surface 132 of the housing 114. The spring loading increases the probe's compliance to the surface of the structure under inspection. Seating of the eddy current sensor 100 over the fastener 84 so that the sensor 100 lies as flat as possible on the structure is generally desirable for conducting a proper inspection. The sensor 100 is retained in the bore 120 with a pin 134 that extends laterally through an opening 136 in the housing wall 126 and passes through a slot 138 in the sensor 100. The proximal side 140 of the slot 138 is blocked by the pin 134 as the spring 130 urges the sensor 100 to withdraw from the bore 120. The proximal side 140 of the slot 138 is located such that the sensor 100 may extend a predetermined distance X from the bore 120 below the distal surface 132 of the housing 114.

In addition, a joint 142 may be provided in the spindle 110 at the connection to the central member 112. The joint 142 may be, for example, a gimbal joint, a ball and socket type joint, or the like, and in the embodiment of a probe 48 described herein, may allow for a deflection of, for example, at least approximately 12 degrees, with a preferred angle of at least 15 degrees between the spindle 110 and the longitudinal axis of the probe 48. Joint deflection may be greater with other embodiments, and particularly in embodiments where the sensor 100 can extend a greater predetermined distance X from the bore 120 below the distal surface 132 of the housing 114 than in the exemplary embodiment described herein.

The joint 142 may be designed to transfer scan rotation through an angle as needed, but to return to a zero angle position when the end is free, which may be referred to as self-aligning. This self-aligning may be accomplished in a variety of ways, for example in a ball and socket type joint, using a non-spherical ball and socket that pulls slightly out and extends an inner spring when an angle away from the longitudinal axis of the probe 48 is created. The spindle 110 and joint 142 rotate during scanning, as does the rest of the probe 48.

In one exemplary embodiment, the inside diameter of the housing 114 is 0.5 inches, the housing wall 126 thickness distally from the central member 112 is 0.112 inches, the radius from the longitudinal axis of the probe 48 to the longitudinal axis of the sensor 100 is 0.183 inches, and the predetermined distance X that the sensor 100 may extend past the distal surface 132 of the housing 114 is 0.008 inches.

The probe materials may include, for example, for the central member 112, spindle 110, spring 130, and pin 134, metals such as steel, stainless steel, or other steel alloy. The housing 114 may be molded plastic or other nonconductive material, which may be translucent to facilitate assembly and visualization of a fastener during scanning. The sensor 100 may be made of materials as known to one of ordinary skill in the art.

Figure 8:
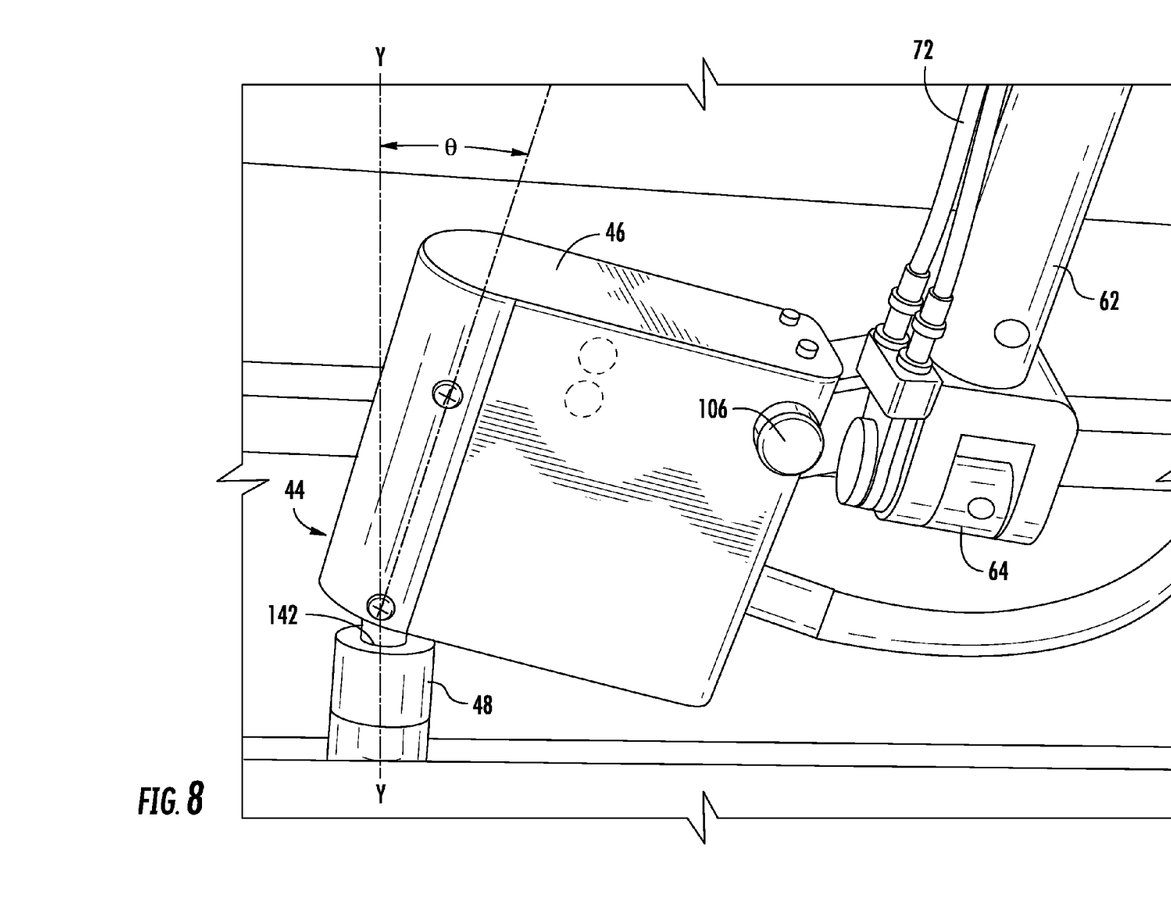
FIG. 8 is a side perspective view of the exemplary scanner including a probe of FIG. 3.

FIG. 8 shows a detail view of the end effector 44 in use. Angle θ is the predetermined deflection angle that the joint 142 provides. As shown, the joint 142 allows a deflection of approximately 15 degrees between the spindle 110 and the longitudinal axis Y-Y of the probe 48. The distance that the sensor 100 can extend past the distal surface 132 of the housing 114 makes this relatively high degree of deflection possible. When the probe 48, and the sensor 100 with it, rotates when the housing 114 is not parallel to the target surface, there will be one point on the path of rotation where the distal surface 132 of the housing 114 is closest to the target, preferably with the sensor 100 touching the target surface, and a point on the opposite side of the path of rotation where the distal surface 132 of the housing 114 is farthest away from the target surface, and without the extension of the sensor 100 lift-off will be experienced. The extending of the sensor 100 past the distal surface 132 of the housing 114 reduces the amount of lift-off or eliminates lift-off, and may keep the sensitivity of the sensor 100 adequate to provide meaningful NDE data over the entire path of rotation. The sensor 100 extending also allows the deflection angle to be increased in the design of the joint 142. An increased available deflection angle facilitates applying and using the probe 48.

Figure 9:
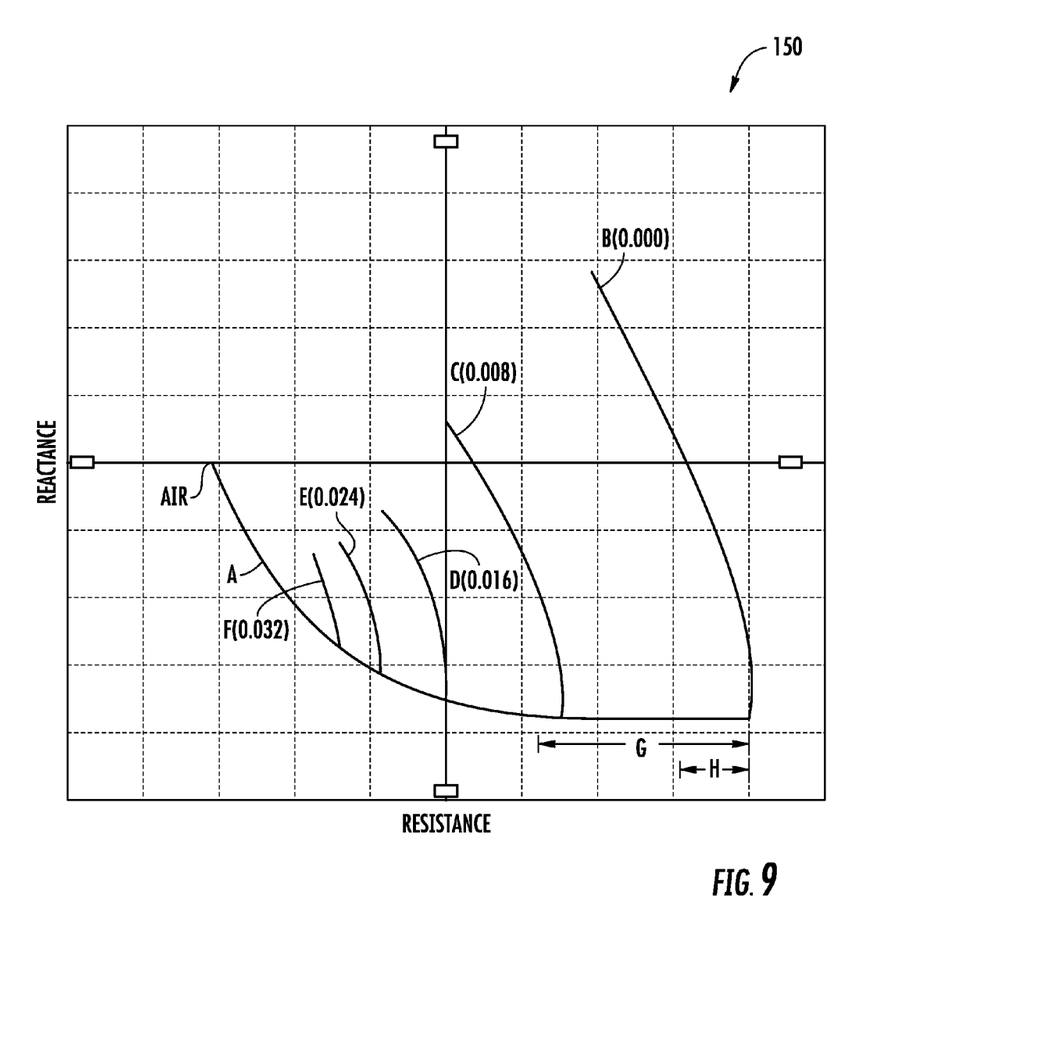
FIG. 9 is an example of a high frequency eddy current impedance plane display that may result from application of the exemplary probe of FIG. 4.

FIG. 9 shows a high frequency eddy current impedance plane display 150 as may result from application of a probe 48 including an eddy current sensor 100. This display 150 may aid an operator/inspector in knowing when the probe 48 is coupled to the structure to allow proper inspection. Resistance is plotted on the X-axis and Reactance is plotted on the Y-axis. The eddy current probe is "nulled" in air, which appears on the display 150 at the far left at the label "AIR" where there is no magnetic field measurement, as opposed to the often used technique of nulling the probe 48 while on the part being inspected, and then, as the probe 48 is brought down over the fastener 84, the eddy current display "dot" comes down to the position where the probe 48 is coupled with the part, which is a stringer in the case shown in FIG. 2.

Curve A in FIG. 9 represents decreasing magnetic field readings from right to left, which corresponds to increased lift-off from right to left. Multiple flaw indications are shown in FIG. 9. These flaw indications are curves B through F, which are each the result of the sensor 100 detecting the same 0.050 inch deep Electrical Discharge Machining (EDM) notch, but with different distances of lift-off. The curves B through F are also labeled with dimensions that designate the distance of lift-off in inches for each of the respective curves. To obtain a desirable 3:1 signal-to-noise ratio (S/N), in testing with the example discussed above in the discussion of FIGS. 4-7, the lift-off of the sensor 100 from the part could not be more than 0.016 inches. Below 0.016 inch lift-off, the probe 48 and structure was considered to be coupled. If the lift-off was greater than this amount, the flaw indication may be detectable, but the S/N was less than desirable and it may become difficult to distinguish a crack in the part from lift-off.

In a test with an eddy current sensor mounted to a probe without a spring to extend the sensor out of the housing, and a spindle with a joint allowing an angle of incidence of 10.5 degrees off of a line perpendicular to the target surface, the dot traveled along curve A approximately within range G as the sensor rotated. With a spring that allowed the sensor to extend 0.008 inches out of the housing, the joint angle could be increased to 15 degrees, and the dot traveled approximately only within range H, providing improved ability to accurately detect flaws.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure. The following claims are in no way intended to limit the scope of the disclosure to the specific embodiments described herein.

What is claimed is:

1. An inspection apparatus, comprising:
   a probe having a longitudinal axis, a first end, and a second, free end defining an opening, wherein the opening is offset from the longitudinal axis;
   a sensor for inspecting a target and providing an electrical output, the sensor received in the opening, wherein when the probe is rotated about the longitudinal axis the sensor moves in a substantially circular path; and
   bias means received in the opening in between the first end of the probe and the sensor to urge the sensor away from the first end of the probe.

2. The inspection apparatus of claim 1, wherein the sensor has a range of movement relative to the probe, and further comprising means for limiting the range of movement to retain part of the sensor in the opening.

3. The inspection apparatus of claim 1, wherein the sensor defines a slot with sides, the probe includes a housing, and the housing includes a wall that defines the opening, and further comprising a pin disposed in the wall and the slot to limit the range of movement of the sensor when a side of the slot bears against the pin, wherein the slot and pin determine a predetermined limit of a range of movement of the sensor out of the opening.

4. The inspection apparatus of claim 1, wherein the sensor has a first end proximate to the bias means and a second end that extends out of the opening when there is no force applied to the second end from outside the opening.

5. The inspection apparatus of claim 1, wherein the second, free end of the probe has a surface, wherein the sensor has a first end and a second end, the first end of the sensor being disposed in the opening proximate to the bias means, and the sensor has an extended position with the second end of the sensor extending away from the surface of the second, free end of the probe a predetermined distance, and a retracted position with the second end of the sensor substantially flush with the surface of the second, free end of the probe.

6. The inspection apparatus of claim 1, further comprising a manipulator arm operatively connected to the first end of the probe, wherein the arm articulates to allow the probe to reach limited access areas.

7. The inspection apparatus of claim 1, further comprising means for rotating the probe about the longitudinal axis such that the sensor moves in the substantially circular path.

8. The inspection apparatus of claim 1, wherein the probe has a longitudinal axis and wherein the probe comprises a gimbal joint or ball and socket type joint between the first end and the second, free end of the probe.

9. The inspection apparatus of claim 8, wherein the probe further comprises a spindle having a proximal end and a distal end, the distal end being operatively connected to the gimbal joint or ball and socket type joint.

10. The inspection apparatus of claim 9, wherein the gimbal joint or ball and socket type joint provides an available deflection between the longitudinal axis of the probe and the spindle of at least approximately 12 degrees.

11. The inspection apparatus of claim 1, wherein the sensor comprises an eddy current sensor, magnetic sensor, or ultrasonic sensor.

12. The inspection apparatus of claim 1, wherein the probe comprises a substantially cylindrical housing with an open end and a wall, and the wall defines a bore that receives the sensor.

13. The inspection apparatus of claim 1, wherein the probe comprises a spindle having a proximal end and a distal end, a central member having proximal end and a distal end, the central member being mounted proximate to the distal end of the spindle, and a substantially cylindrical housing mounted to the central member, and wherein the housing includes a wall, extends distally from the central member, and defines an opening adapted to fit over the end of a fastener, and the wall defines the opening for receiving the sensor.

14. The inspection apparatus of claim 13, wherein the probe has a longitudinal axis and further comprises a joint between the first end and the second, free end of the probe, the joint being operatively connected with the spindle and providing available deflection of the probe longitudinal axis from the spindle in any direction of at least approximately 15 degrees.

15. An inspection apparatus, comprising:
a probe having a longitudinal axis, a first end, and a second, free end having a surface and defining an opening, wherein the opening is offset from the longitudinal axis the probe including a gimbal joint or ball and socket type joint disposed between the first end and the second, free end of the probe and a spindle having a proximal end and a distal end, the distal end being operatively connected to the gimbal joint or ball and socket type joint;
a sensor for inspecting a target and providing an electrical output, the sensor having a first end and a second end, the sensor being received in the opening, wherein when the probe is rotated about the longitudinal axis, the sensor moves in a substantially circular path, and wherein the sensor has a range of movement relative to the probe;
bias means received in the opening in between the first end of the probe and the first end of the sensor to urge the sensor away from the first end of the probe;
means for limiting the range of movement to retain part of the sensor in the opening;
wherein the sensor has an extended position with the second end of the sensor extending away from the surface of the second, free end of the probe a predetermined distance, and a retracted position with the second end of the sensor substantially flush with the surface of the second, free end of the probe.

16. The inspection apparatus of claim 15, wherein the direction of the range of movement of the sensor is parallel to the longitudinal axis of the probe.

17. A method of performing an inspection, comprising:
providing a probe having a longitudinal axis and including a first end and a second, free end defining an opening, wherein the opening is offset from the longitudinal axis, with bias means first inserted in the opening and then a sensor for inspecting a target and providing an electrical output inserted in the opening;
urging the sensor away from the first end of the probe using the bias means; and
rotating the probe about the longitudinal axis to cause the sensor to move in a substantially circular path.

18. The method of performing an inspection of claim 17, further comprising limiting the range of movement of the sensor to retain part of the sensor in the opening and allow part of the sensor to extend out of the opening.

19. The method of performing an inspection of claim 17, wherein a manipulator arm is operatively connected to the first end of the probe, further comprising articulating the arm to allow the probe to reach limited access areas.

20. The method of performing an inspection of claim 17, wherein the probe includes a gimbal joint or ball and socket type joint between the first end and the second, free end of the probe and a spindle operatively connected to the gimbal joint or ball and socket joint, the method further comprising:
providing available deflection of the probe longitudinal axis from the spindle of at least approximately 15 degrees.

* * * * *